United States Patent [19]

Sturman et al.

[11] Patent Number: 5,411,492
[45] Date of Patent: May 2, 1995

[54] HYPODERMIC NEEDLE PROTECTOR

[76] Inventors: Martin Sturman, 7315 Granite Rd., Melrose Park, Pa. 19126; Maurice Kanbar, 4 E. 77th St., New York, N.Y. 10021; Robert J. Cohn, 61 Sterling Ave., Dallas, Pa. 18612; Albert Kolvites, R.R. 3 Box 117A Yeager Rd., Mountaintop, Pa. 18707

[21] Appl. No.: 270,677
[22] Filed: Jul. 5, 1994
[51] Int. Cl.⁶ .............................................. A61M 5/32
[52] U.S. Cl. ...................... 604/263; 604/198; 128/919
[58] Field of Search ............... 604/198, 263, 110, 187, 604/192; 128/919

[56] References Cited

U.S. PATENT DOCUMENTS

| | | | |
|---|---|---|---|
| 4,573,976 | 3/1986 | Sampson et al. | 604/263 X |
| 4,915,696 | 4/1990 | Feimer | 604/263 X |
| 5,201,708 | 4/1993 | Martin | 604/110 |
| 5,215,534 | 6/1993 | DeHarde et al. | 604/198 |

*Primary Examiner*—John D. Yasko
*Attorney, Agent, or Firm*—Michael Ebert

[57] ABSTRACT

A safety hypodermic needle and shielding cap assembly attachable to a standard syringe adapted to prevent the needle after it has been injected in a patient and then withdrawn, from accidental sticking the operator. The syringe includes a fluid chamber provided at its front end with a projecting nozzle surrounded by a cylindrical socket. The assembly includes a hollow hub receivable in the syringe socket and a needle mounted on the hub and extending along its longitudinal axis whereby the nozzle projects into the hub to deliver fluid to the needle. Mounted adjacent one side of the hub is a short track on which is slidable a flexible push rod on whose upper end is laterally attached a shielding cap having a center bore in alignment with the needle. In the operating mode of the assembly, the push rod is retracted and the cap is then telescoped on the hub to expose the needle for injection into a patient. In the shielding mode of the assembly, in effect after the needle is withdrawn from a patient, the push rod is extended by the operator to raise the cap bore above the tip of the needle whereby the cap then shields the tip. Should pressure be applied accidentally to the shielding cap seeking to force it toward the needle, the cap which is cantilevered from the track by the flexible rod will then swing to an offset position in which the bore is out of line with the needle tip.

9 Claims, 3 Drawing Sheets

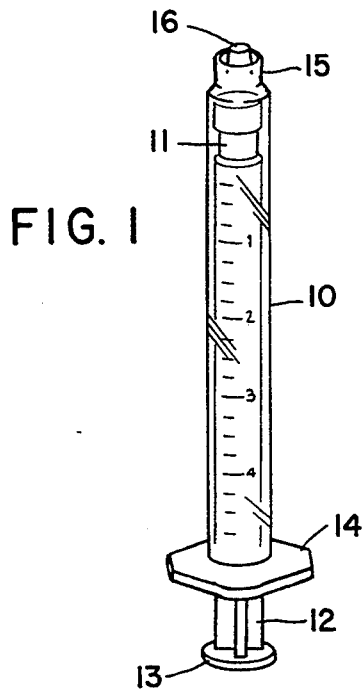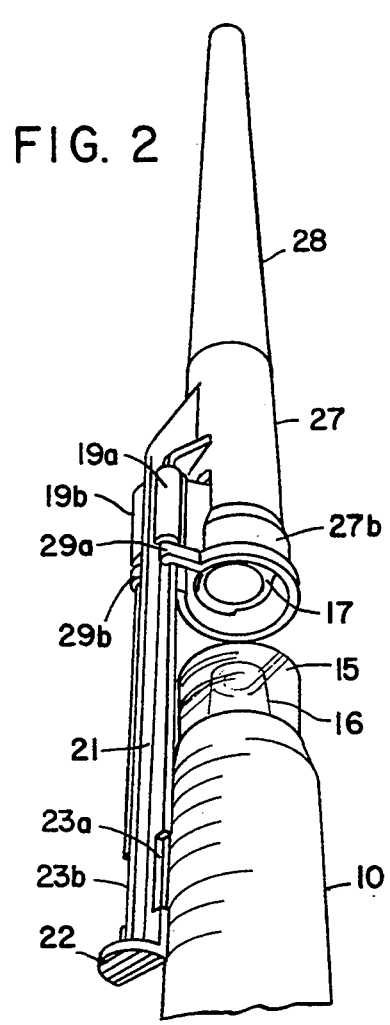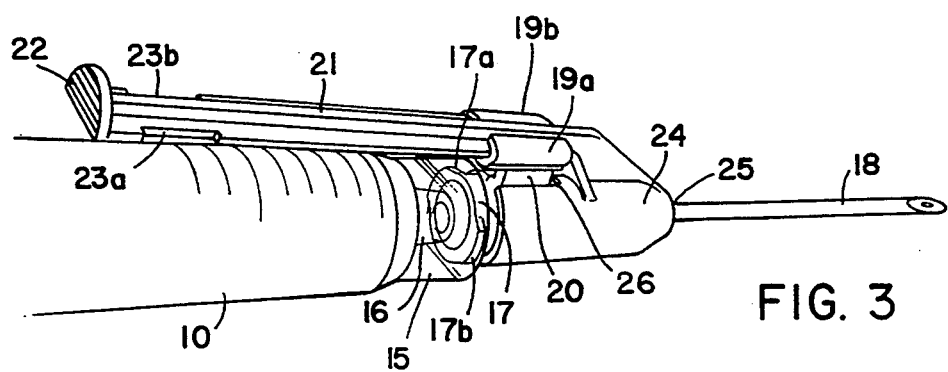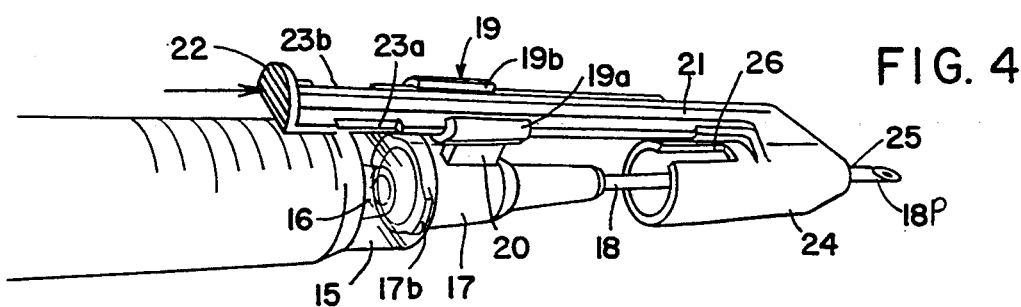

HYPODERMIC NEEDLE PROTECTOR

BACKGROUND OF INVENTION

1. Field of Invention

This invention relates generally to hypodermic syringes, and in particular to a safety hypodermic needle and shielding cap assembly, which in an operating mode permits an operator to inject the needle into a patient, and which after the needle is withdrawn from the patient, is switched to a shielding mode in which the point of the needle is shielded to prevent accidental sticks thereby.

2. Status of Prior Art

A hypodermic needle is usable for intravenous, subcutaneous and intramuscular injection of fluids, or the removal of blood (venipuncture), body fluids or abnormal collections thereof, the needle being of hollow contruction and having a slanted open point. When the needle is mounted on a syringe, it is adapted to aspirate or inject fluids for diagnostic or therapeutic purposes.

Disposable hypodermic needles are now mass produced at low cost, many billions of such syringes being used every year in the health care field. While the modern hypodermic syringe now includes a fluid chamber molded of synthetic plastic material rather than glass, its basic design remains much as it was in 1853 when invented by Charles Pravaz, a French physician.

In a hypodermic syringe of standard design, a piston is slidable within a cylindrical fluid chamber, the shank of the piston extending beyond the rear end of the chamber and terminating in a handle. The front end of the chamber is provided with a projecting nozzle that is coaxial with an internally-threaded socket adapted to receive a needle-supporting hub. When the hub is screwed into the socket, the nozzle is then projected therein to communicate with the needle.

A hypodermic needle and a syringe attached thereto are distributed in sterile condition within a plastic bubble package to protect them against contamination in storage and shipment. In addition, the needle is enclosed in a removable overcap whose inlet end snaps onto the needle hub. Thus, after the hypodermic needle and syringe are removed from its package, in order to put it to use, one must first remove the overcap to expose the needle. After the hypodermic syringe has been injected into a patient and then withdrawn, it is the usual practice, before discarding the syringe, to place the overcap back on the needle hub so that those thereafter handling discarded syringes for purposes of disposal will not be pricked thereby.

When a sterile hypodermic needle is injected into a patient suffering from hepatitis or other infectious diseases and the needle is then withdrawn from the patient, it may be contaminated with infectious agents. Hence, should the handler inadvertently prick himself with this contaminated needle, the consequences may be serious.

The possibility of accidental contamination by needle puncture of the skin of those individuals in the health care field who employ hypodermic syringes for venipuncture, the withdrawal of body fluids or for any other medical purpose is fairly high and represents a significant risk. Thus, physicians, nurses, laboratory personnel, paramedics and others involved in the care and treatment of patients are in danger of being accidentally inoculated with infectious microorganisms by contaminated needles.

Most accidental needle sticks occur when the needles are being recapped, for to do so properly, one must first align the needle with the relatively small diameter inlet of the overcap. Should the needle be misaligned, as may well happen should the handler be careless, distracted or fatigued, the point of the needle will not enter the overcap but may instead puncture the finger of the handler.

It is well established that the risks involved in handling hypodermic syringes has markedly increased in recent years. Statistics indicate very high rates of hepatitis B infection among medical and laboratory personnel by reason of this accidental mode of disease transmission. Medical personnel who care for patients suffering from AIDS run a still higher risk; for a needle contaminated with HIV (Human Immunodeficiency Virus) is a source of great danger. Should the handler of this needle be accidentally punctured, he faces the prospect of contracting a disease currently having a 100% mortality rate as compared, say, to the 5 to 10% mortality rate of hepatitis B.

The 1988 patent to Wanderer et al., U.S. Pat. No. 4,731,059 is concerned with preventing needle sticks, and for this purpose provides a shield which is slidable from a position covering the needle to a position overlying the fluid chamber so that the needle can be exposed when put to use and thereafter shielded. A somewhat similar arrangement is disclosed in the 1987 patent to Fox, U.S. Pat. No. 4,695,274, which shows a retractable safety jacket for a hypodermic needle.

One practical problem with the safety shields or needle guards of the type disclosed in the Wanderer et al. and Fox patents is that when the needle is exposed so that the syringe can be put to use, the retracted guard then covers and obscures the transparent chamber which is graduated so that one can determine the amount of fluid that is contained therein. Hence this guard interferes with the proper operation of the hypodermic syringe.

But the more serious drawbacks of these prior art needle guard arrangements is that in order to accommodate the guard, they require a modification of the basic configuration of the standard hypodermic syringe. Thus in one commercially available form of safety hypodermic syringe having a needle guard, the needle is mounted on an elongated extension tube projecting from the fluid chamber, so that when the guard is retracted, it overlies the extension tube, not the fluid chamber. Hence, fluid from the chamber must be conducted through the extension tube which, by its very nature, elongates the hypodermic syringe, making it more difficult to handle.

To provide a safety hypodermic needle and shield assembly that is compatible with a standard syringe, the patent to Spier et al. U.S. Pat. No. 4,921,490, and the patent to Sturman et al., U.S. Pat. No. 4,863,435, disclose an assembly having a needle-supporting hub whose hollow base is coupled to the socket of the syringe so that the projecting nozzle then communicates with the needle.

Anchored on this hub and surrounding the needle extending therefrom is a helical spring at whose upper end is a shield, the length of the spring being such as to place the shield in front of the needle point. In the retracted mode of the assembly, the spring is compressed and latched to expose the needle so that it can be injected into a patient. In the operative mode of the assembly, which takes effect after the needle is withdrawn from the patient and the spring is released, the shield is then placed in front of the needle point to prevent accidental sticks.

The safety needle and shield assemblies disclosed in the Spier et al. and Sturman et al. patents have distinct advantages, for they require no modification of the standard syringe. But they have practical drawbacks. One such drawback is that the latching mechanism which releases the spring is so bulky that it prevents injection of the hypodermic needle into a patient at a low angle, as is sometimes necessary. Another drawback is that when the assembly is in its operative position, it may still be possible to compress the spring and cause the needle to pass through the protective shield and prick the handler.

Our prior 1993 U.S. Pat. No. 4,246,427 provides a safety hypodermic needle and shielding cap assembly for a standard syringe. The assembly includes a needle-supporting hub whose hollow base is coupled to the socket of the syringe, the nozzle then communicating with the needle. Encircling the hub and attached thereto is a resilient actuator collar defining an annular space within which is received the lower end of a helical spring surrounding the needle extending from the hub. The upper end of the spring is received in the cavity of a shielding cap having a center bore herein through which the needle is passable.

The cap is tethered by opposing lines of unequal length to the collar. In the retracted mode of the assembly, the spring is compressed by the cap, which is provided with a pair of opposed lugs that are inserted in corresponding slots in the long sides of the collar, thereby latching the cap and exposing the needle, so that it can be injected into a patient. After the needle is withdrawn, the assembly is put in its extended mode by squeezing the collar at its short sides to disengage the lugs and release the cap which is carried by the expanding spring to a position covering the needle point, the tether lines of unequal length acting to cant the cap to offset its bore with respect to the needle point.

An assembly of the type disclosed in our prior patent, though effective for its intended purpose, is relatively expensive to manufacture, for the inclusion of a helical spring in the assembly adds substantially to manufacturing costs.

SUMMARY OF INVENTION

In view of the foregoing, the main object of this invention is to provide a safety hypodermic needle and shielding cap assembly for a syringe which obviates the danger of an operator thereof being accidentally pricked by the point of the needle after it has been injected in a patient and then withdrawn.

More particularly, an object of this invention is to provide a safety hypodermic needle and shielding cap assembly of the above type which requires no basic modification of the design of a standard syringe and which can be manufactured inexpensively on a mass production basis.

A significant advantage of an assembly in accordance with the invention is that it entails no spring, as in our prior assembly and is therefore less costly to manufacture.

Still another object of the invention is to provide an assembly of the above type which when coupled to a standard syringe, can be held and manipulated by a single hand of the operator, the assembly when switched from its operating mode to its shielding mode then producing a tactile sensation and an audible click indicative of this switch, making it unnecessary for the operator to check on whether the needle is then safe.

A salient feature of the invention is that in the shielding mod of the assembly in which the cap covers the point of the needle, should the cap then be subject to a force seeking to depress it, the cap will then be canted so that the center bore therein is offset with respect to the needle point, and the point cannot pass through the bore.

Yet another object of the invention is to provide an assembly of the above type having a low profile, making it possible to inject the needle into a patient at a low angle relative to the body surface of the patient.

Briefly stated, these objects are accomplished by a safety hypodermic needle and shielding cap assembly attachable to a standard syringe adapted to prevent the needle, after it has been injected in a patient and then withdrawn, from accidental sticking the operator. The syringe includes a fluid chamber in which a piston is slidable, the chamber being provided at its front end with a projecting nozzle surrounded by a cylindrical socket.

The assembly includes a hollow hub receivable in the syringe socket and a needle mounted on the hub and extending along its longitudinal axis whereby the nozzle projects into the hub to deliver fluid to the needle. Mounted adjacent one side of the hub is a short track in which is slidable a flexible push rod on whose upper end is laterally attached a shielding cap having a center bore in alignment with the needle. In the operating mode of the assembly, the push rod is retracted and the cap is then telescoped on the hub to expose the needle for injection into a patient. In the shielding mode of the assembly, in effect after the needle is withdrawn from a patient, the push rod is extended by the operator to raise the cap bore above the tip of the needle whereby the cap shields the tip. Should pressure be applied accidentally to the shielding cap seeking to force it toward the needle, the cap which is cantilevered from the track by the flexible rod will then swing to an offset position in which the bore is out of line with the needle tip.

BRIEF DESCRIPTION OF DRAWINGS

For a better understanding of the invention as well as other objects and further features thereof, reference is made to the following detailed description to be read in conjunction with the accompanying drawing, wherein:

FIG. 1 illustrates a standard hypodermic syringe;

FIG. 2 shows a safety hypodermic needle and shielding cap assembly in accordance with the invention in relation to the nozzle end of a standard syringe;

FIG. 3 illustrates the assembly coupled to the syringe, with the overcap of the assembly removed to expose the needle;

FIG. 4 illustrates the assembly in the process of switching from its operating mode to its shielding mode;

DESCRIPTION OF INVENTION

Figure 5:
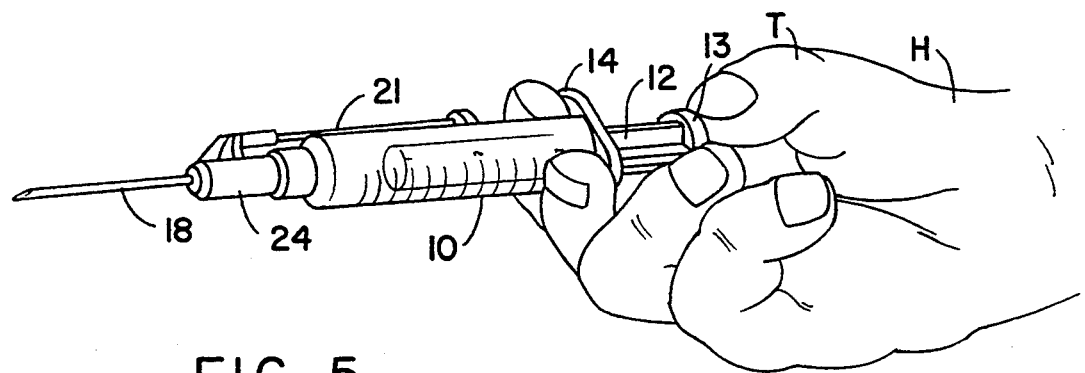
FIG. 5 shows the assembly held by an operator's hand in its operating mode in condition for injection.

Referring now to FIG. 1, there is shown a standard hypodermic syringe usable with a safety hypodermic needle and shielding cap assembly in accordance with the invention.

Included in the syringe is a cylindrical fluid chamber 10 formed of transparent, synthetic plastic material such as polyethylene, polypropylene, polystyrene or PVC having indicia thereon to indicate the level of fluid in the chamber. Slidable within the chamber is a piston 11 for ejecting fluid from the chamber or drawing fluid therein, the piston having a shank 12 which extends beyond the open end of the chamber and terminates in a handle 13.

As is conventional, the rear end of chamber 10 is provided with a flange 14 so that to manipulate the piston to draw fluid from a patient or to inject fluid into the patient, the user holds the flange with the fingers of one hand while grasping handle 13 with the fingers of the other hand. At the front end of chamber 10 is an internally-threaded cylindrical socket 15, and coaxially disposed therein is a nozzle 16 whose inlet communicates with the interior of the chamber.

As shown in FIGS. 2 and 3, a safety hypodermic needle and shielding cap assembly in accordance with the invention includes a hollow hub 17 having at its lower end a pair of teeth 17A and 17B which project from diametrically-opposed positions. These teeth act as an external thread to engage the internal threading on the coupling socket 15 of the syringe, this Leur-lok arrangement makes it possible to mount the assembly on the syringe.

Supported on hub 17 and extending axially therefrom is a hypodermic needle 18 the lower open end of which is disposed within the hub cavity. When, therefore, hub 17 is screwed into socket 15 of the syringe, nozzle 16, coaxially disposed within the socket, projects into the hub cavity to communicate with the needle so that fluid taken from a patent may be fed into the fluid chamber by the needle, or fluid from the chamber fed into the needle.

Mounted on one side of hub 17 in parallel relation to the longitudinal axis of the hub which extends through needle 18 is a short track formed by a pair of flexible side rails 19A and 19B, anchored on a rectangular projection 20 integral with hub 17. Side rails 19A and 19B are inwardly biased to press against a push rod 21 which is slidable along the track. The push rod is formed of flexible plastic material and terminates at its lower end in a finger rest 22. Rod 21 is indented on either side adjacent finger rest 22 to provide a pair of opposing detent notches 23A and 23B. The notch dimensions correspond to those of side rails 19A and 19B of the track. Hence when push rod 21 is shifted along the track to a position in which side rails 19A and 19B register with the detent notches, the side rails then snap into these notches and thereby arrest further movement of the rod in either direction.

Laterally supported on the upper end of push rod 22, as best seen in FIGS. 3 and 4, is a generally cylindrical plastic shielding cap 24, having a conical crown at whose peak is a center bore 25 normally in line with hypodermic needle 18. In the operating mode of the assembly which is illustrated in FIG. 3, push rod 21 is retracted with respect to the track, and shielding cap 24 is then telescoped on hub 17, thereby fully exposing needle 18. Cap 24 is provided with a longitudinal slot to accommodate hub projection 20 to permit the cap to telescope on the hub.

FIG. 2 illustrates the assembly before it is coupled to syringe 10, the assembly then including a protective overcap having an upper conical section 28 which surrounds needle 18 and a lower cylindrical section 27 which surrounds hub 17. Lower section 27 is provided with a base 27B of enlarged diameter and a longitudinal slot therein to permit its dilation. Also provided is a pair of spring fingers 29A and 29B extending laterally from either side of the slot. These fingers embrace push rod 21 just below side rails 19A and 19B of the track on which the rod is slidable. Hence the overcap cannot then be pulled off the assembly.

When the assembly is coupled to syringe 10 so that the teeth 17A and 17B at the lower end of hub 17 screw into the coupling collar 15 of the syringe, the collar 15 then enters the annular space between base 27B of the lower section 27 of the overcap and the hub 17 disposed within base 27B, causing base to dilate and in doing so to disengage spring fingers 29A and 29B from the push rod and the push rod track 19A and 19B.

Thus it is only when the assembly is joined to the syringe that it then becomes possible to slip the overcap off the assembly to expose the needle 18. When the assembly includes the overcap, it is then in a storage mode, and when the assembly is joined to the syringe and the overcap is slipped off, the assembly is then in its operating mode.

When the assembly is packaged so that it can be shipped or stored, the protective overcap is then latched in place. It is only after the assembly is taken out of its sterile package by an operator and then joined to syringe 10, that it becomes possible to slip off the overcap so that the assembly is then, as shown in FIG. 3, in its operating mode in condition to be injected in a patient.

In order to switch the assembly to its shielding mode in which shielding cap 24 then surrounds the point of the needle, push rod 21 must be advanced from its retracted position, as shown in FIG. 3, to an extended position. FIG. 4 illustrates an intermediate stage in the advance of the push rod by the thumb of the operator engaging finger rest 22. As the operator pushes the rod forward with his thumb while grasping the syringe with his fingers, shielding cap 24 then moves away from hub 17 along needle 18 whose point projects through the center hole 25 of the cap. It is only when the push rod is fully extended and locked, that the point of the needle then lies within the shielding cap, and the assembly is in its shielding mode.

In summary, when the overcap covers the hub and the needle mounted thereon, and the shielding cap is telescoped on the hub, it is then in a storage mode. When the assembly is joined to the syringe and the overcap removed, the assembly is then in the operating mode in condition for injection. And when the needle is withdrawn from the patient and its point covered by the shielding cap, it is then in its shielding mode.

Operation

Figure 6:
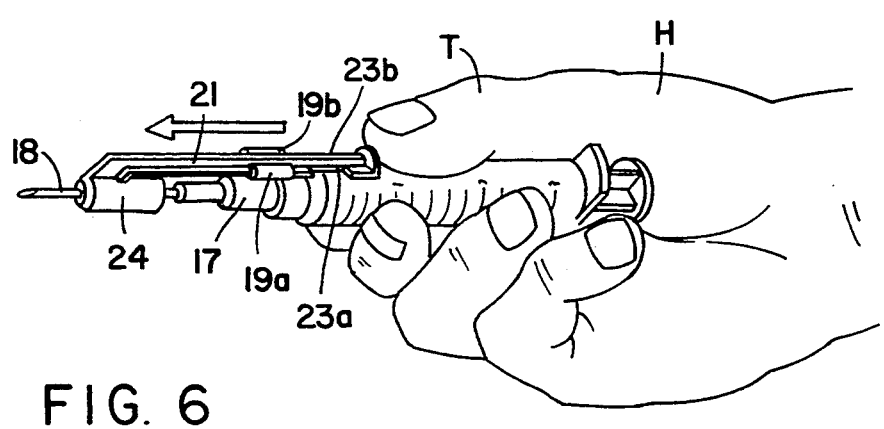
FIG. 6 shows the assembly held by an operator after injection whose finger is pushing the assembly into the shielding mode.
Figure 7:
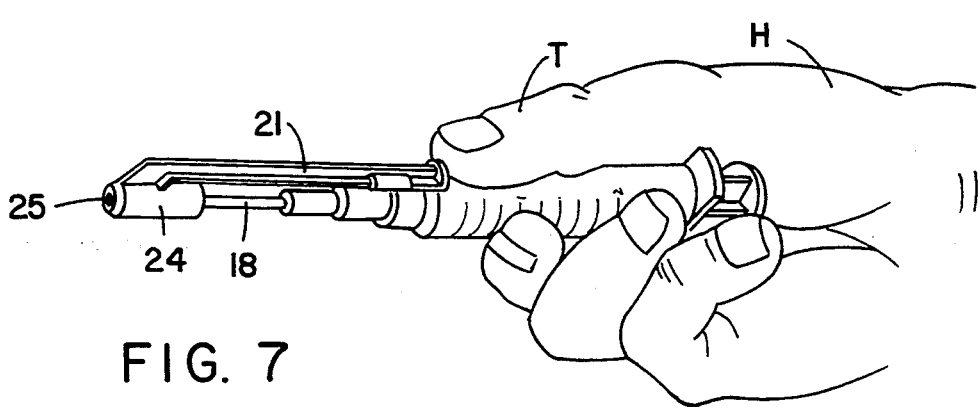
FIG. 7 shows the assembly in its shielding mode.

FIGS. 5 to 7 illustrate the assembly coupled to syringe 10, the syringe being grasped by the curled fingers of a hand H of the operator whose thumb T then engages finger rest 22. A significant advantage of an assembly in accordance with the invention is that it makes possible a one handed operation for injecting the needle into a patient in the operating mode of the assembly and for quickly protecting the needle point after it is withdrawn from the patient to avoid accidental sticks.

FIG. 5 shows the assembly coupled to syringe 10 in its operating mode in condition for injection into a patient. The hand H of an operator which holds the syringe has two fingers engaging flange 14 of the syringe and thumb I pushing handle 13 to advance the piston in the syringe chamber.

Figure 5A:
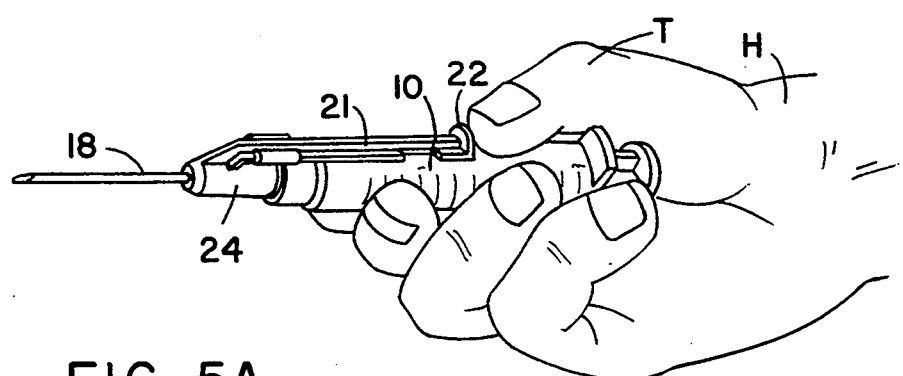
FIG. 5A shows the assembly in the operator's hand after the needle has been withdrawn from the patient.

FIG. 5A shows the assembly in the hand H of the operator in its operating mode just after the needle 18 has been withdrawn from the patient in which it had been injected. It is at this stage that the danger of accidental needle prick arises, for the needle withdrawn from the patient is contaminated and an accidental prick with this needle may have serious consequences.

It will be noted in FIG. 5A, that the thumb T of the operator's hand is pressed against the finger rest 22 of push rod 21. To switch from the operating mode to the shielding mode, the operator, as shown in FIG. 6 pushes push rod 21 with his thumb T, thereby causing push rod 21 to slide forward with respect to rails 19A and 19B of the track mounted on one side of hub 17 supporting needle 18. As the push rod moves forward, shielding cap 24 moves along the needle. FIG. 6 shows an intermediate stage in the extension of push rod 21, the point of the needle still projecting from the center bore of the shielding cap and being exposed. FIG. 7 shows the assembly in its shielding mode, for now push rod 21 is fully extended and shielding cap 24 protectively surrounds the point of needle 18, the tip of which is below the center bore 25 of the cap.

It is important to note that when rod 21 is fully extended, the tensioned side rails 19A and 19B of the track then snap into the detent notches 23A and 23B of the rod and permanently latch the rod so that it is not thereafter possible to advance or retract it. This snap action produces an audible click and also a tactile sensation felt by the thumb, telling the operator that the assembly is in its shielding mode, and making it unnecessary to check to be sure this is the case.

A typical doctor or nurse handling the assembly often works under conditions of stress and may, therefore, not have the opportunity to visually check to see if the safety mechanism has been activated. But with the audible click and the tactile sensation produced by the snap action of the flexible side rails, these positive indications make a check unnecessary.

Double Protection

Figure 8:
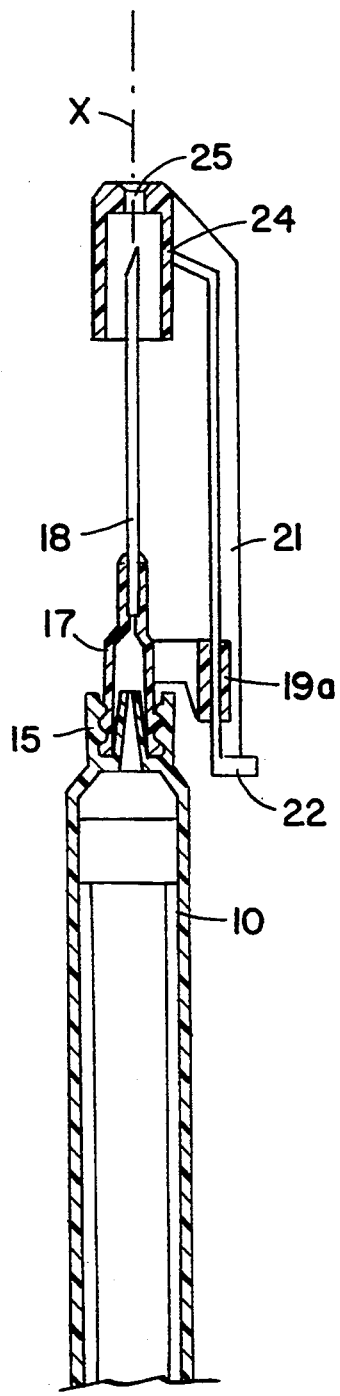
FIG. 8 is a sectional view of the assembly in its shielding mode.

FIG. 8 schematically illustrates the safety hypodermic needle and shielding cap assembly mounted on syringe 10 in its shielding mode in which shielding cap 24 protectively surrounds the point of needle 18 which is in line with the longitudinal axis X passing through the center bore 25 in the cap, the bore now being above the tip of the needle. The cap is protected from being displaced to expose the needle by the permanently latched push rod.

Figure 9:
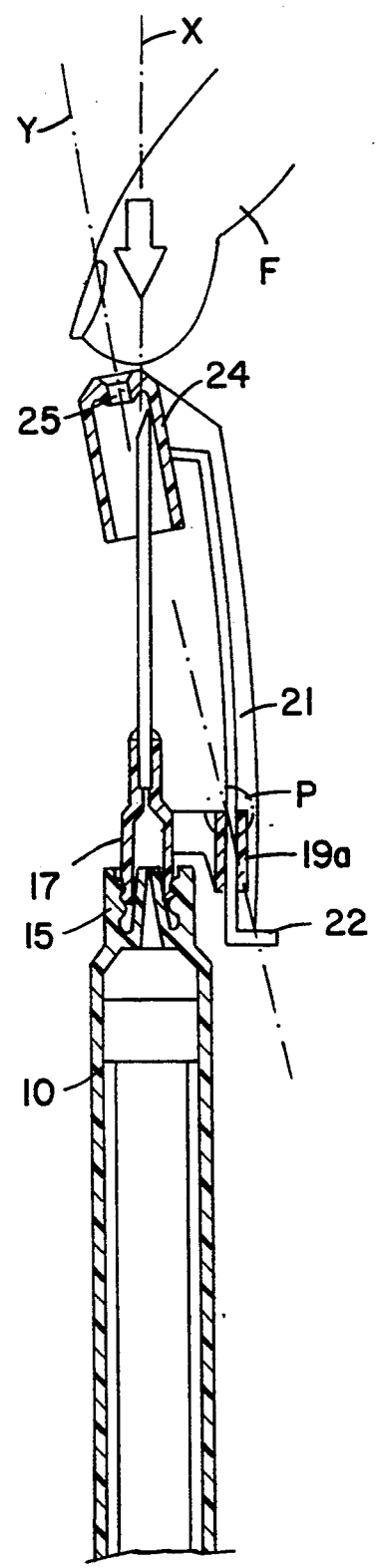
FIG. 9 shows the assembly in its shielding mode, the shielding cap being subjected to finger pressure.

FIG. 9 schematically illustrates why any force which seeks to push shielding cap 24 down toward hub 17 of the assembly will not be effective. This force will not cause center hole 25 of the cap to admit the tip of the needle so that the cap could then ride down the needle and expose its contaminated point. The reason cap 24 cannot be pushed down by the force applied by a finger F, and double protection is afforded, is that cap 24 is cantilevered by flexible push rod 21 from the side rails 19A and 19B of the track, so that push rod is pivoted on the track at point P. When therefore a downward force is applied to cap 24, it will cause the cap to swing sideways with respect to the needle.

Hence the center bore 25 of the cap is then in line with an axis Y which is at an acute angle with respect to longitudinal axis X. Should the pressure applied to the cap being such that to force the cap down, the needle point will engage the crown of the cap to one side of center bore 25, and the point will jam into the crown which is a relatively thick material.

If the assembly in its shielding mode is accidentally dropped on its cap end, and the resultant force on impact is sufficient to unlatch the push rod, the cap has already been driven off center in relation to the needle point, and the needle will then jam into the crown of the cap.

It is to be noted that the structure of the assembly has a low profile which was best seen in FIG. 3, hugs one side of syringe 10. The advantage of this low profile over a more bulky needle protector is that it is often necessary to inject a patient at a low angle, and a bulky mechanism would make such injection difficult or impossible to carry out.

While there has been shown a preferred embodiment of the invention, many modifications may be made therein without departing from the essential spirit of the invention.

We claim:

1. A safety hypodermic needle and shielding cap assembly adapted to be coupled to a standard syringe having a fluid chamber provided at one end with a projecting nozzle surrounded by a coupling collar; said assembly comprising:
A. a hollow hub receivable in the socket of the syringe and having a needle mounted therein provided with a tapered point extending along a longitudinal axis passing through the hub whereby the nozzle is projected into the hub and is in fluid communication with the needle;
B. a short track mounted on one side of the hub in parallel relation to said axis;
C. a push rod of flexible material slidable on the track and terminating at its lower end in a finger rest which when engaged by a finger of an operator advanced the rod from a retracted to an extended position;
D. a shielding cap laterally mounted at the upper end of the rod and have a crown provided with a center bore in line with said axis, the cap when the rod is retracted being telescoped on the hub to expose the needle whereby the assembly is then in an operating mode in condition to inject a patient, the cap when the rod is extended surrounding the point of the needle whereby the assembly is then in a shielding mode to prevent accidental sticks.

2. An assembly as set forth in claim 1, in which the hollow hub, the track and the cap are all fabricated of synthetic plastic material.

3. An assembly as set forth in claim 1, in which the coupling collar is internally threaded and the hub is provided at a base thereof with a pair of opposed teeth which engage the collar.

4. An assembly as set forth in claim 1, in which the track is formed by a pair of flexible side rails which are biased to engage opposite sides of the push rod.

5. An assembly as set forth in claim 1 in which the rails are anchored on a rectangular projection integral with the hub.

6. An assembly as set forth in claim 5, in which the cap is provided with a longitudinal slot to accommodate the projection when the cap is telescoped on the hub.

7. An assembly as set forth in claim 4, in which the rod is provided adjacent the finger rest with a pair of opposed detent notches, the side rails snapping into these notches when the rod is extended in the shielding mode.

8. An assembly as set forth in claim 1, further including an overcap to cover the needle and the hub in a storage mode before the assembly is put to use.

9. An assembly as set forth in claim 8, in which the overcap is provided with a pair of spring fingers which engage the rod to prevent the overcap from being pulled off the assembly.

* * * * *